J. YOUNG.

2 Sheets—Sheet 1.

Electro-Magnetic Bathing Apparatus.

No. 1,711.

Reissued June 28, 1864.

Witnesses.

Minis Livingston

D. W. Coombs

Inventor

James Young

J. YOUNG. 2 Sheets—Sheet 2.
Electro-Magnetic Bathing Apparatus.
No. 1,711. Reissued June 28, 1864.
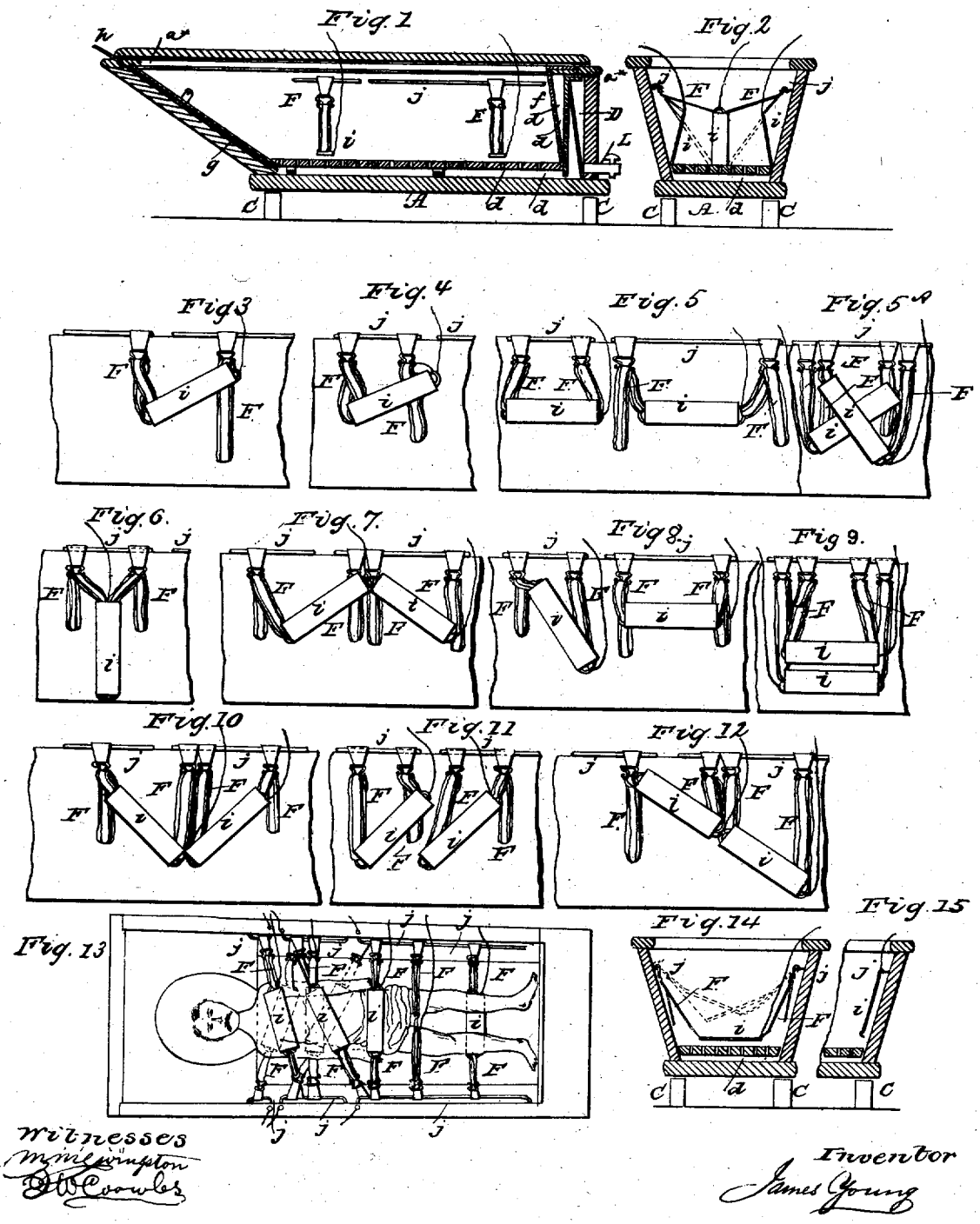
Witnesses
M. M. Livingston
D. W. Crowley
Inventor
James Young

UNITED STATES PATENT OFFICE.

JAMES YOUNG, OF NEW YORK, N. Y.

IMPROVEMENT IN ELECTRO-MAGNETIC BATHING APPARATUS.

Specification forming part of Letters Patent No. 32,332, dated May 14, 1861; Reissue No. 1,711, dated June 28, 1864.

*To all whom it may concern:*

Be it known that I, JAMES YOUNG, of the city of New York, county of New York, and State of New York, have invented a new and Improved Electro-Magnetic Bathing Apparatus; and I do hereby declare that the following is a full, clear, and exact description of the same, reference being had to the accompanying drawings, forming a part of this specification, in which—

Figure 1:
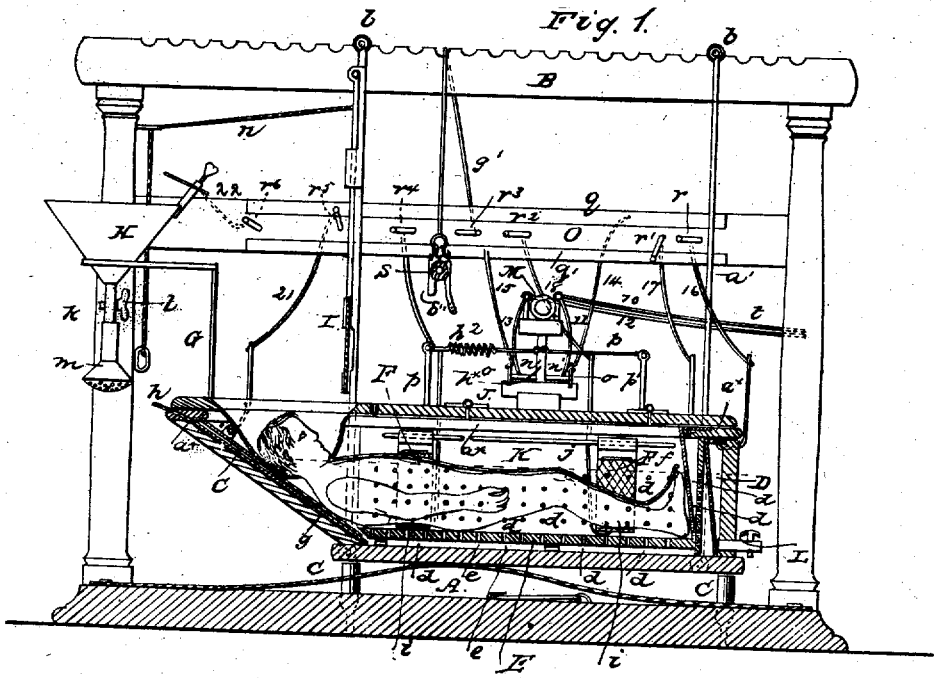
Figure 2:
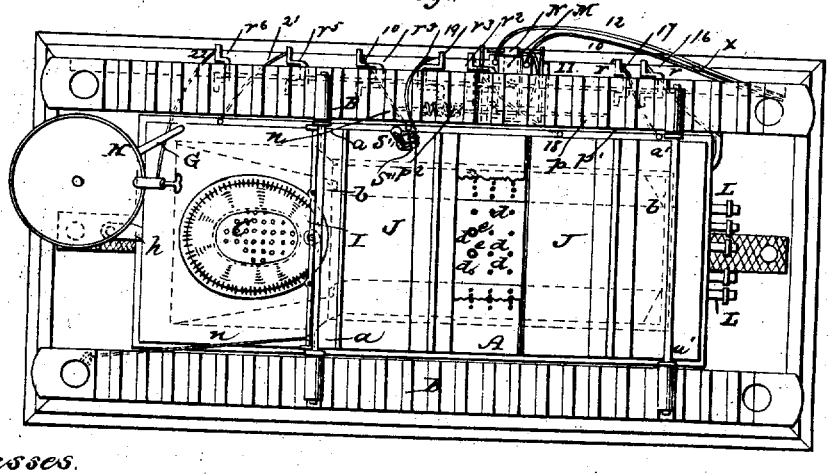

Figure 1 represents a longitudinal vertical section of my invention. Fig. 2 is a plan or top view of the same. Fig. 1′ represents a longitudinal vertical section, more clearly illustrating the electrodes. Figs. 2′ and 14′ and 15′ represent transverse sections. Figs. 3′, 4′, 5, 5^A, &c., represent the different positions that the electrodes may be placed in.

Similar letters of reference in all the figures indicate corresponding parts.

The nature of my invention consists in the employment of adjustable metallic plates, which are charged with positive or negative electricity, or may be left uncharged, at the will of the operator, by means of apparatus hereinafter described, whereby I am enabled at will to concentrate and apply electricity readily and effectively to any given part of the body, or subject the whole body to its influence at one and the same moment, while lying in a non-conducting bath-tub.

The superiority of my invention consists in my ability, by means of it, to concentrate at will and apply electricity readily and effectively to any given part of the body, or to subject the whole body to its influence at one and the same moment, as above stated; and also in the fact that while applying electricity in the manner indicated less time and labor are required of the operator, and at the same time the body of the patient is left untrammeled and unconfined in its movements while in the bath, yet open to the simultaneous application of heated air, vapor, or water, medicated or non-medicated, as may be deemed desirable. This tub A may be suspended from rods *a a′*, which connect with rock-shafts *b*, the ends of which are insulated by surrounding them with glass or any other non-conductor of electricity. Said rock-shafts have their bearings on the upper notched surface of longitudinal timbers B, or they may be arranged in any other manner, providing a good hold for the same and convenient for changing their position is obtained.

By changing the position of the rock-shafts the entire tub may be raised or lowered, or one end may be raised and the other lowered, as the convenience of the patient may require. If the tub is suspended from the rock-shafts *b* a swinging motion can be imparted to the same without impairing its insulation, and its oscillations are kept within certain limits by an elastic strap attached to its bottom; and if it is desired to have the tub stationary it may be fastened by a hook or lowered on the posts *c*, which are made of glass or some other non-conductor in order to preserve the insulation of the tub.

Rails *a** are attached to the top of the sides of the tub, extending and projecting over inside and outside—inside to prevent the water splashing over on the operator or on the floor, on the outside to form a hand-rail, useful to the patients' hands to help themselves in or out of the tub, or sit upon the same to be dried off by themselves or by an attendant. This top rail is a very essential part of my invention, since without it, in administering an electric bath, paralyzed patients are liable to make a wave and splash the water out on the floor, and to make the feet of the operator damp, whereby a sort of connection between the operator and the heavy charge in the tub is created, consequently the operator will receive a very heavy annoying shock, often laming both arms and causing them to be very weak for two or three weeks. Now, with the use of this top rail, at the end of a day's bathing of eighteen patients the floor is as dry in the evening as it was in the morning.

The tub is provided with a metallic head-plate or electrode, C, and with a foot-plate or electrode, D, and a jacket, E, may or may not be placed in the interior of the tub, as clearly shown by Fig. 1 on the drawings. The sides of this jacket are perforated with a number of small holes, *d*, to admit steam, air, or water, and those holes which pass through the wooden sides of the jacket may be protected by metallic eyes *e*, to prevent holes becoming ragged and enlarged by the manipulation necessary to cleanse the tub.

The foot-plate *f* of the jacket E is also constructed of metal or some other good conductor of electricity, and it may be perforated with a number of small holes, the same as the head-plate C of the tub, and both the foot-plates of the jacket and of the tub may be inclined or perpendicular from the bottom up, so as to conform to the position of the feet of the patient while influenced by electricity.

The metallic head-plate C of the tub is placed in an inclined position, as clearly shown by Fig. 1 on the drawings, and it terminates a little above the bottom of the tub, and it is elevated above the head of the tub, so as to leave a space, *g*, between it and the head of the tub. This space communicates with the space between the jacket and the tub, so that the steam, air, or water surrounding the jacket finds its way under the head-plate C, and through the holes in the same to the head of the patient.

A slide, *h*, which passes down behind the head-plate, serves to cut off communication between the space around the jacket and the space behind the head-plate C, so that the head of the patient can be exposed to the direct action of the steam or air, or protected from the same, as may be deemed necessary.

As regards any part or parts of the body lying between the electrodes or head and foot-plates C and D, they may be treated locally by properly arranging and electrically charging the adjustable metallic plates or electrodes *i i'*, so that a current of electricity can be passed laterally or across the body, as through from lung to lung or side to side, or perpendicularly through the body, as from abdomen to spine; also diagonally, as from the right shoulder to the left knee, as indicated in some forms of rheumatism and neuralgia; obliquely, as from the liver to and through the spleen, or from the back brain to and through the genital organs.

The rails *j j* may each be charged with electricity by means of suitable connections and binding-posts, and the plates *i i* may be charged from thence secondarily, which in some cases would be preferable, and thus the various currents may be distributed to and through the body by and through the medium of these adjustable metallic plates or electrodes *i i'*.

Another mode of using the plates *i i'* is to dispense with the straps, buckles, and clamps shown in Figs. 1', 2, 3', 4', &c., and instead give each end of each plate or electrode *i i'* a kink or bend, so that each plate can be clamped or hooked directly onto the metallic guides or rails *j j'*, and the connection thus formed will convey the electric current on down into the bath and through the steam or water to the patient. (See Fig. 15'.)

The guides or rails *j j'* are necessary or useful to hold or sustain in position the plates or electrodes *i i'*. These guides or rails may be of any form convenient for holding the electrodes *i i'*. One mode is to make these rails or guides tramways of metal, and in lieu of the clamps which hold the ends of the electrodes *i i'* to the guides friction-rollers may be used, and the plates or electrodes *i i'* may be fastened directly to these friction-rollers.

Other modes may also be used involving the same general principle of holding, guiding, and charging the metal plates or electrodes *i i'*, the result being the same. The novelty at this point, however, is the use of the metallic rails or guides to the electrodes *i i'* in any direction with the ability to charge the guides or plates.

There may be secured to the edge of the tub and near its head a standard, G, bent at right angles, and provided with a ring or socket to secure the funnel-shaped vessel H. This vessel terminates in a tube, *k*, which is provided with a stop-cock, *l*, to the end of which a rose, *m*, of any desired form and construction may be attached. The object of this vessel is to treat in particular the eyes, ears, or other portions of the head of the patient with magnetized water, hot, cold, or tepid.

The standard G is so arranged that the vessel H can be turned over the head of the patient, or may be turned back out of the way when not needed.

A fan, I, attached to the rods *a* and operated by means of a cord, *n*, passing through a loop that is secured to the wall, serves to cool the head of the patient in case such cooling is found necessary, as in fever, or in hot climates.

When air or vapor is used in this apparatus the tub A is provided with a cover, J, made in several sections, and that section nearest the head of the tub is provided with an aperture to admit the head of the patient.

In cases where a water-bath is applied the body of the patient is protected by a woolen blanket, K, covered with oil-cloth, keeping comfortable every part of the patient's body. The water, steam, vapor, or hot air is admitted to the tub through one of the faucets L.

The connection of the bathing apparatus with the battery, and its operation, is as follows:

The positive pole of the battery connects by means of a wire, 10, with one end of the outer wire of an electro-magnet, M, of any desired form and construction, and the other end of this wire connects through a wire, 11, with one arm of the switch N. The negative pole of the battery connects by a wire, 12, with one end of the inner wire of the electro-magnet, and the other end of this wire connects by the wire 13 with the other arm, *n*, of the switch N'. The switch N operates between two poles, *o o'*, and it is operated by a cord, *p*, which is connected to two standards, *p'*, that are secured to the side of the tub A. This cord passes through two loops, *p**, on the top or end of a standard, *p'**, which rises from the switch, and a spring, $p^2$, serves to keep the cord taut. If an oscillating motion is now imparted to the tub the friction of the cord in the loop *p** causes the switch to partake of the motion of the tub, and the arms *n n'* are alternately brought in contact with the plates *o o'*. The plate *o'* connects through a wire, 14, with a metal strip, *q*, and the plate *o* connects in the same manner through a wire, 15, with a metal strip, *q'*. Both these strips are attached to a slat, *o*, of wood or other non-conducting material, which may be arranged in any convenient place or position, maintaining suitable connection to all or any of the metallic plates or electrodes in the bath-tub A. The slat *o* forms the bearings for the brakes $r$, $r'$, $r^2$, $r^3$, $r^4$, $r^5$, and $r^6$, which serve to pass the current through the whole or through certain parts of the body of the patient. The brakes $r$ connect through the wire 16 with the foot-plate D of the tub A. The brake $r'$ connects through the wire 17 with the foot-plate *f* of the jacket E. The brake $r^2$ connects through the wire 18 with the adjustable plate or electrode *i*, which serves to treat the legs or any desired part of the body of the patient. The brake $r^3$ connects through the wire 19 with a metal ball, *s*, inclosed in a sponge, *s'*, or with a catheter, *s''*, or with other similar devices for rubbing or treating certain parts of the human body. The brake $r^4$ connects through the wire 20 with the adjustable plate or electrode *i*. The brake $r^5$ connects through the wire 21 with the head-plate C of the tub, and the brake $r^6$ connects through the wire 22 with the funnel-shaped vessel H.

If it is desired to pass a current through the whole body of the patient the brake $r^5$ is turned upon the strip *q* and the brake $r'$ is turned down on the strip *q'*, as shown in Fig. 1 on the drawings, and the switch N is turned so as to bring the arms *n* and *n'* in contact with the plates *o'* and *o*. The current will now pass through the wires 10 11 14, and through the strip *q* and wire 21 to the plate C, thence through the liquid contained in the tub and through the body of the patient to the foot-plate *f*, and through the wire 17, strip *q'*, through wires 15, 13, and 12 back to the negative pole of the battery. If an oscillating motion is now imparted to the tub the switch N is changed, and the arm *n'* comes in contact with the plate *o'*, and the arm *n* in contact with the plate *o*, and the current passes through the wires 10, 11, and 15 to the strip *q'*, thence through the wire 17 to the foot-plate *f*, and through the body of the patient to the head-plate C, and through the wire 21, strip *q*, and wires 14, 13, and 12 back to the battery.

When the tub A is stationary and resting on the insulating bottles *c* or non-conducting legs, then the switch N may be disconnected from the cord *p* and be removed by hand at the will of the operator. Thus all desirable changes can be made as well when stationary as when oscillating; besides, when the tub is oscillating the switch N can be moved as well as the brakes $r$, $r'$, $r^2$, $r^3$, &c., can be moved by hand at the will of the operator, without interference from the motion of the tub.

The funnel-shaped vessel H is brought into the current by turning the brake $r^6$ upon the strip *q* and turning off the brake $r^5$. The contents of said vessel will now be directed on the afflicted parts of the head by turning the faucet *l*, and the current passes through said contents and the body of the patient to the foot-plate *f*, and through the wire 17, strip *q'*, and through wires 15, 13, and 12 back to the battery.

In some cases it may be desirable to rub certain portions of the body or to treat those parts which can only be reached by a catheter or by other similar instruments, and in order to produce the desired effect the brake $r^3$ is turned on, so as to bring the wire 19 into the current. Thus it will be seen that by changing the polarity of the stationary magnetic plates C and D, or the adjustable magnetic plates or electrodes *i i'*, the electrical current can be directed through the whole length of the body of the patient, or through any part of the body, as the will of the operator may direct, or as the disease, whether general or local, may require.

Having thus fully described my invention, what I claim, and desire to secure by Letters Patent, is—

1. The use of the above-described electrodes *i* and *i'*, charged and operated in the manner and for the purposes hereinbefore specified.

2. The use of adjustable metallic plates or electrodes *i i'*, in combination with stationary metallic plates or electrodes C and D connected with an electro-magnet, in combination with a non-conducting bath-tub, for the purpose specified.

3. The combination of the bathing-tub A, an electro-magnet, metallic strips *q q'*, and brakes $r$, $r'$, $r^2$, $r^3$, $r^4$, $r^5$, and $r^6$, for the purpose of charging at will each or all of the metallic plates or electrodes in the tub A, and operating substantially as described.

4. The combination of a non-conducting bath-tub, with a metallic plate or electrode at each end, one electrode being connected with a positive pole and the other electrode with a negative pole of an electro-magnet.

5. The use of the main switch *n n'*, by which the polarity of all the brakes $r$, $r'$, $r^2$, $r^3$, $r^4$, $r^5$, and $r^6$ are at once reversed and by one movement.

6. The combination of an electro-magnet M, bathing-tub A, and metallic vessel H with a rose *m*, operating as and for the purpose set forth.

7. So combining a swinging tub, A, switch N, and an electro-magnet, M, that by the oscillating motions of the tub the current is changed.

8. So arranging the top rail, *a**, on the sides of the tub that the same projects over the inside and outside, in the manner and for the purposes set forth.

9. The stationary metallic guides or side rails, *j j'*, attached to the side or top rails of a bath, when used for maintaining in position, guiding, or charging with electricity the electrodes *i i'*, substantially as described.

JAMES YOUNG.

Witnesses:
H. E. MYER,
R. E. MIX.